United States Patent
Alrayyes et al.

(10) Patent No.: US 12,318,787 B1
(45) Date of Patent: Jun. 3, 2025

(54) DEVICE FOR AUTOCLAVING AND CENTRIFUGING A SAMPLE

(71) Applicant: KING SAUD UNIVERSITY, Riyadh (SA)

(72) Inventors: Yasser Fahad Alrayyes, Riyadh (SA); Rayan Bakur Alkurdi, Riyadh (SA); Reham Nasser Al Jasser, Riyadh (SA); Ahmed Ibrahim Alzahrani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/069,597

(22) Filed: Mar. 4, 2025

(51) Int. Cl.
  *B04B 15/02* (2006.01)
  *A61L 2/00* (2006.01)
  (Continued)

(52) U.S. Cl.
  CPC ............ *B04B 15/02* (2013.01); *A61L 2/0023* (2013.01); *A61L 2/24* (2013.01); *B04B 5/0414* (2013.01);
  (Continued)

(58) Field of Classification Search
  CPC ........ A61L 2/00; A61L 2/0005; A61L 2/0011; A61L 2/0023; A61L 2/24; A61L 2202/00; A61L 2202/10; A61L 2202/12; A61L 2202/122; A61L 2202/14; A61L 2202/20; A61L 2202/22; B04B 5/00; B04B 5/04; B04B 5/0407; B04B 5/0414; B04B 7/00; B04B 7/02; B04B 15/00; B04B 15/02
  See application file for complete search history.

(56) References Cited

U.S. PATENT DOCUMENTS 4,286,748 A * 9/1981 Bailey ...................... B04B 1/02
  494/35
10,427,171 B2  10/2019 Thorwid et al.
  (Continued)

FOREIGN PATENT DOCUMENTS

| CN | 117380408 A | 1/2024 |
|---|---|---|
| WO | 2022223210 A1 | 10/2022 |
| WO | 2023198544 A1 | 10/2023 |

OTHER PUBLICATIONS

Zheng, Xijiao, et al. "Exploration of proper heating protocol for injectable horizontal platelet-rich fibrin gel." International Journal of Implant Dentistry 8.1 (2022): 36.

*Primary Examiner* — Natasha E Young
(74) *Attorney, Agent, or Firm* — Nath, Goldberg & Meyer; Joshua B. Goldberg

(57) ABSTRACT

A device for autoclaving and centrifuging a sample includes a main housing having a housing base, an isolation unit above the housing base, and an interior chamber. The isolation unit is defined by an automated pipe system housed within the sidewalls of the housing. The isolation unit surrounds at least a portion of the interior chamber. A water tank is disposed within a side wall of the main housing and is in communication with the isolation unit. A centrifuge extends from the centrifuge base and into the interior chamber. The centrifuge can include a centrifuge base, a centrifuge sample insert detachably connected to the base, and a centrifuge motor extending through the centrifuge base and the centrifuge sample insert. A computerized control panel is in communication with the automated pipe system.

15 Claims, 5 Drawing Sheets

(51) Int. Cl.
*A61L 2/24* (2006.01)
*B04B 5/04* (2006.01)
*B04B 7/02* (2006.01)

(52) U.S. Cl.
CPC ........... *B04B 7/02* (2013.01); *A61L 2202/122* (2013.01); *A61L 2202/14* (2013.01); *A61L 2202/22* (2013.01)

(56) References Cited

U.S. PATENT DOCUMENTS

| | | |
|---|---|---|
| 10,799,886 B2 | 10/2020 | Bathelt et al. |
| 2011/0319248 A1 | 12/2011 | Starbard |
| 2013/0026684 A1* | 1/2013 | Romero De La Mora ................... B29C 41/06 264/503 |
| 2019/0060915 A1* | 2/2019 | Liang .................... B04B 5/0421 |
| 2023/0010107 A1 | 1/2023 | Liberti |

* cited by examiner

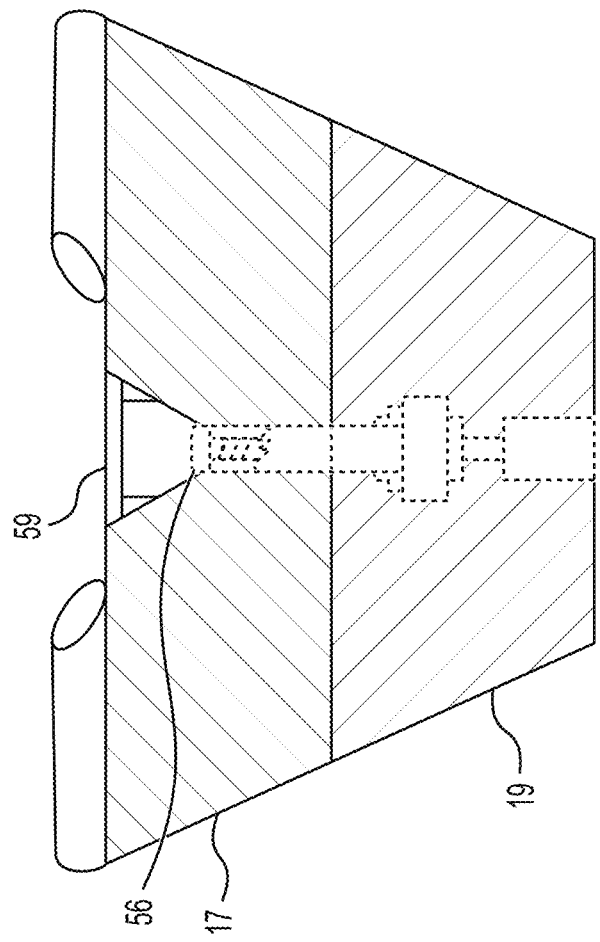
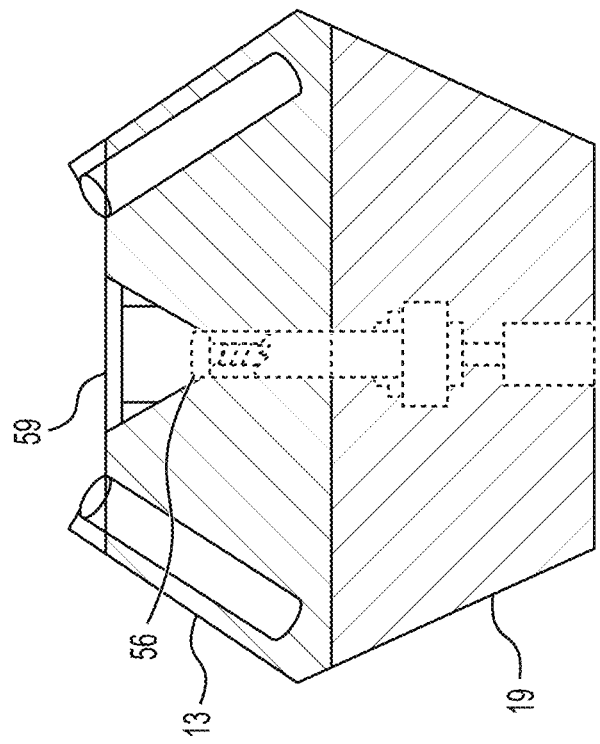
FIG. 4B
FIG. 4A

DEVICE FOR AUTOCLAVING AND CENTRIFUGING A SAMPLE

BACKGROUND

1. Field

The present disclosure relates to a device for centrifuging and autoclaving a sample and, particularly, to a device for preparing an autoclaved platelet-rich fibrin (PRF).

2. Description of the Related Art

With the current surge of autogenous materials in the medical field, one widely used material is platelet-rich concentrates such as platelet-rich fibrin (PRF). PRF is a material that is created by centrifuging the blood into three zones based on density, platelet-poor plasma (PPP), platelet-rich fibrin clot (PRF), and red blood cells (RBCs). PRF has been used as a barrier membrane in numerous medical fields due to its beneficial effects. It harbors many proteins that suppress the secretion of pro-inflammatory cytokines such as Interleukin 1 beta (IL-1β), tumor necrosis factor-alpha (TNF-α), and Interleukin 6 (IL-6). Similarly, PRF has also shown a pro-angiogenic effect, as it can enhance the release of vascular endothelial factor (VEGF), transforming growth factor β1 (TGF-β1), and platelet-derived growth factor (PDGF) hence, improving wound healing.

The preparation of Platelet-Rich Fibrin (PRF) typically involves a meticulously controlled process designed to extract the fibrin clot, which is rich in platelets and growth factors, from a patient's blood. This process involves one of various precise protocols with different rotational speeds, durations, and angulations to ensure the quality and efficacy of the final product. The first step in this process is the collection of venous blood from the patient. A sterile syringe or a vacuum tube is used to dispense blood into specialized tubes. These tubes are typically made of glass or silica-coated plastic to encourage clot activation, as PRF formation relies on the natural coagulation process. Anticoagulants must not be added, as their presence would inhibit clot formation.

Blood collection should be done immediately before centrifugation to minimize the risk of premature clotting or degradation. Once the blood is collected, it is subjected to centrifugation. The tubes are placed in a centrifuge in a balanced configuration to ensure proper operation. The centrifugation protocol depends on the type of PRF being prepared, either as the standard PRF protocol or modified PRF protocols. The centrifuge is set to a specific speed, measured in revolutions per minute (RPM), runs for a defined duration, and in a specific angulation. These parameters are carefully selected to achieve the optimal relative centrifugal force (RCF) necessary for separating the blood into its components. For example, the standard PRF protocol produces a fibrin clot rich in platelets, leukocytes, and growth factors. The RPM typically ranges between 2700 and 3000 RPM (200-400×g. RCF) and the centrifugation duration is usually 8-12 minutes.

In a modified PRF protocol that can enhance the distribution of growth factors and cellular content within the fibrin matrix, the RPM typically ranges between 1300 and 1500 RPM (150-200×g. RCF) and the centrifugation duration is usually 10-14 minutes. Another example of a modified PRF protocol that produces a liquid PRF that can be injected into tissue includes an RPM of approximately 60×g. and the centrifugation duration is usually 3-5 minutes. Care must be taken to ensure a smooth deceleration phase, as sudden stops can disrupt the separation of the blood layers. There are various other protocols that can be found in the literature. The user has the freedom to choose a specific protocol based on the clinical scenario and their preference.

After centrifugation, the blood separates into three distinct layers: platelet-poor plasma (PPP) at the top, the platelet-rich fibrin (PRF) clot in the middle, and red blood cells (RBCs) at the bottom. Proper centrifugation settings are critical to achieving a clear separation of these layers, with the PRF forming a dense fibrin clot just above the RBC layer. The PRF must be extracted carefully to avoid contamination with the adjacent layers. The PRF clot is then harvested using sterile tools, such as forceps or scissors. The PPP layer is first removed to expose the PRF layer. Careful attention is required during this step to ensure that the PRF is not mixed with the underlying RBC layer, which could compromise its quality.

Once isolated, the PRF clot is ready for further processing. The PRF clot can be used directly or processed into membranes for specific applications. To create membranes, the PRF is gently compressed using sterile gauze or mesh to extract any remaining plasma while preserving its fibrin structure. This process should be carried out promptly after centrifugation to maintain the bioactivity of the platelets and growth factors. Conventionally, the centrifugation is done at room temperature (20-25° C.) and at atmospheric pressure. To produce an autoclaved platelets-rich concentrate, however, additional control of heat and pressure, reaching temperatures up to 134° C. or 273° F. and pressures up to 15 to 30 psi, is required.

Although PRF has many advantages, it still comes with a significant drawback which is its fast resorption rate that prevents it from becoming an ideal barrier membrane for some clinical situations. PRF has been reported to last from 2 to 3 weeks. Several recent studies have demonstrated that PRF resorption rate could be significantly extended to more than 4 months by heating. Heat-treating the blood using hot steam generated from autoclaving simultaneously while centrifugating it into PRF can prolong degradation and enhance the mechanical properties of the resulting PRF. However, prolonging the time between blood withdrawal, centrifugation, and heating can harm PRF's effectiveness, leading to lesser beneficial effects.

There is an urgent need for a device that can minimize the time between blood withdrawal, centrifugation, and heating to avoid harming PRF's effectiveness.

Thus, a device for autoclaving and centrifuging a sample solving the aforementioned problems is desired.

SUMMARY

The present subject matter relates to a device for autoclaving and centrifuging a biological sample, such as but not limited to blood. In an embodiment, the device can heat-treat a blood sample using hot steam while simultaneously centrifuging the blood sample, thereby limiting the duration needed to produce an autoclaved Platelet-Rich Fibrin (PRF). In another embodiment, the device can be used to autoclave various materials, such as medical devices and instruments.

In an embodiment, a device for autoclaving and centrifuging a sample can include a main housing having a housing base, an isolation unit above the housing base, and an interior chamber. The isolation unit is defined by an automated pipe system housed within sidewalls of the main housing. The isolation unit surrounds at least a portion of the interior chamber. A water tank is disposed within a side wall of the main housing and is in communication with the isolation unit. A centrifuge extends from the centrifuge base and into the interior chamber. The centrifuge can include a centrifuge base, a centrifuge sample insert detachably connected to the base, and a centrifuge motor extending through the centrifuge base and the centrifuge sample insert. A computerized control panel is in communication with the automated pipe system.

In an embodiment, a device for autoclaving and centrifuging a sample can include a main housing having a housing base, an isolation unit above the housing base, and an interior chamber. The isolation unit is defined by an automated pipe system housed within sidewalls of the main housing. The isolation unit surrounds at least a portion of the interior chamber. A water tank is disposed within a side wall of the main housing and is in communication with the isolation unit. A centrifuge extends from the centrifuge base and into the interior chamber. The centrifuge can include a centrifuge base, a centrifuge sample insert detachably connected to the base, and a centrifuge motor extending through the centrifuge base and the centrifuge sample insert. A computerized control panel is in communication with the automated pipe system. In an embodiment, the interior chamber includes a thermometer in communication with the computerized control panel.

These and other features of the present subject matter will become readily apparent upon further review of the following specification.

BRIEF DESCRIPTION OF THE DRAWINGS

FIG. 4A is a cross-sectional view of a vertical centrifuge.

FIG. 4B is a cross-sectional view of a horizontal centrifuge.

DETAILED DESCRIPTION OF THE PREFERRED EMBODIMENTS

Figure 1:
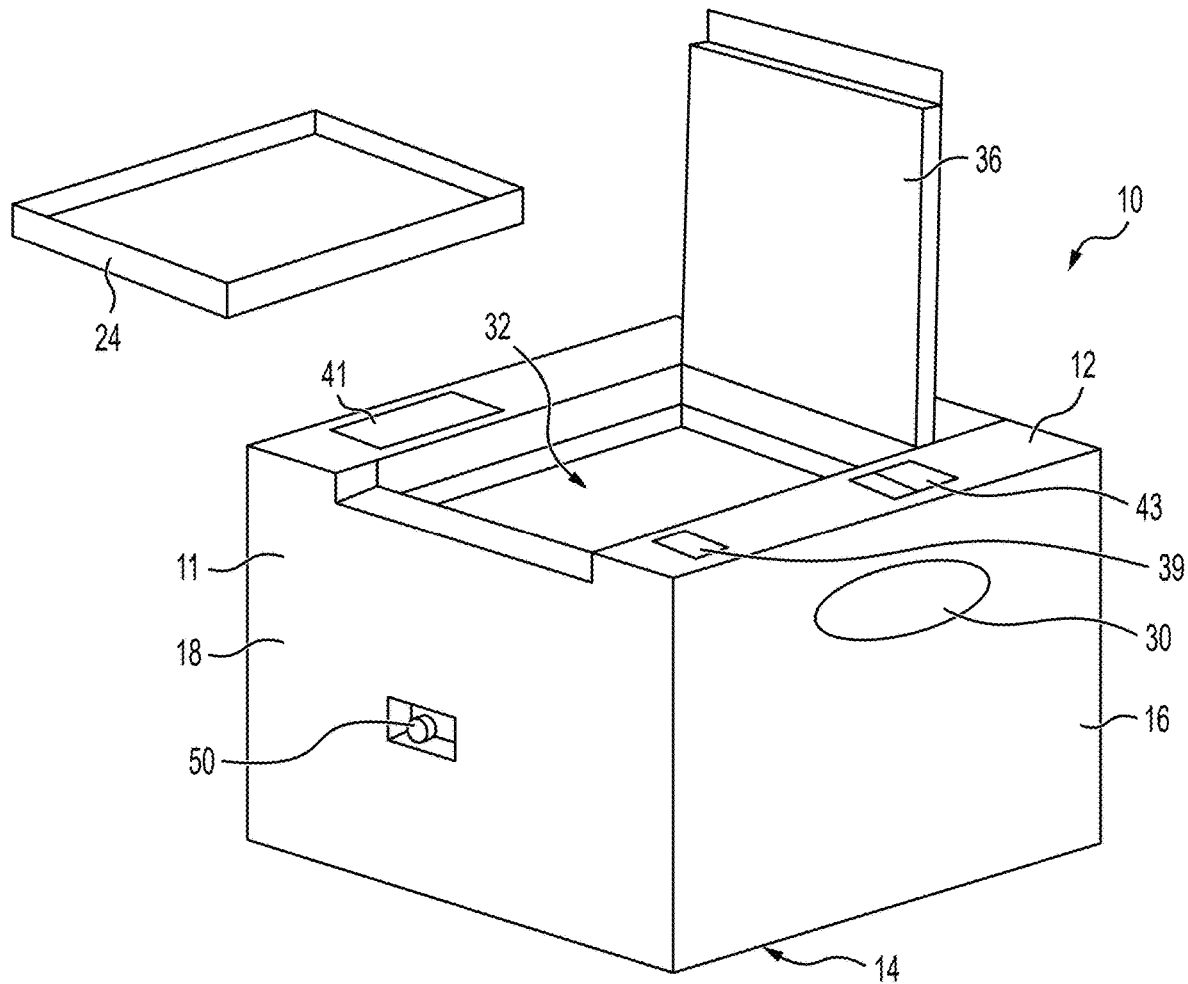
FIG. 1 is a perspective view of the device for autoclaving and centrifuging a sample.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

Figure 2:
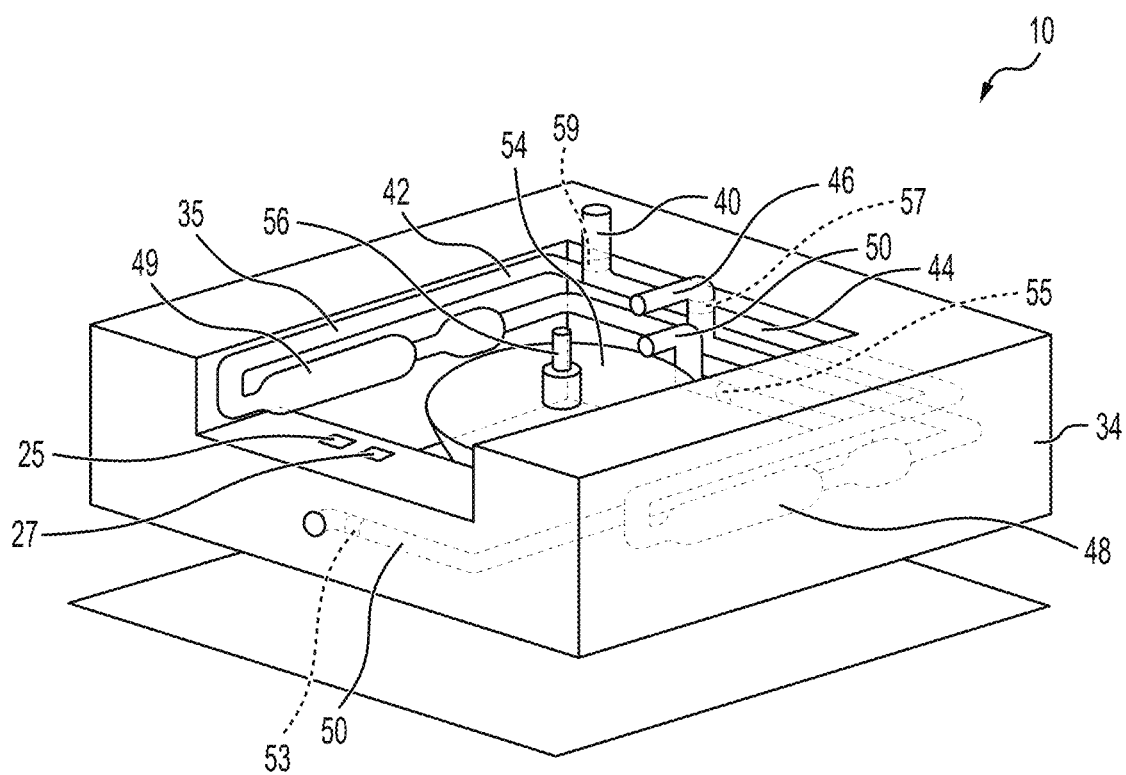
FIG. 2 is a transparent view of the isolation unit and base of the device for autoclaving and centrifuging a sample.
Figure 3:
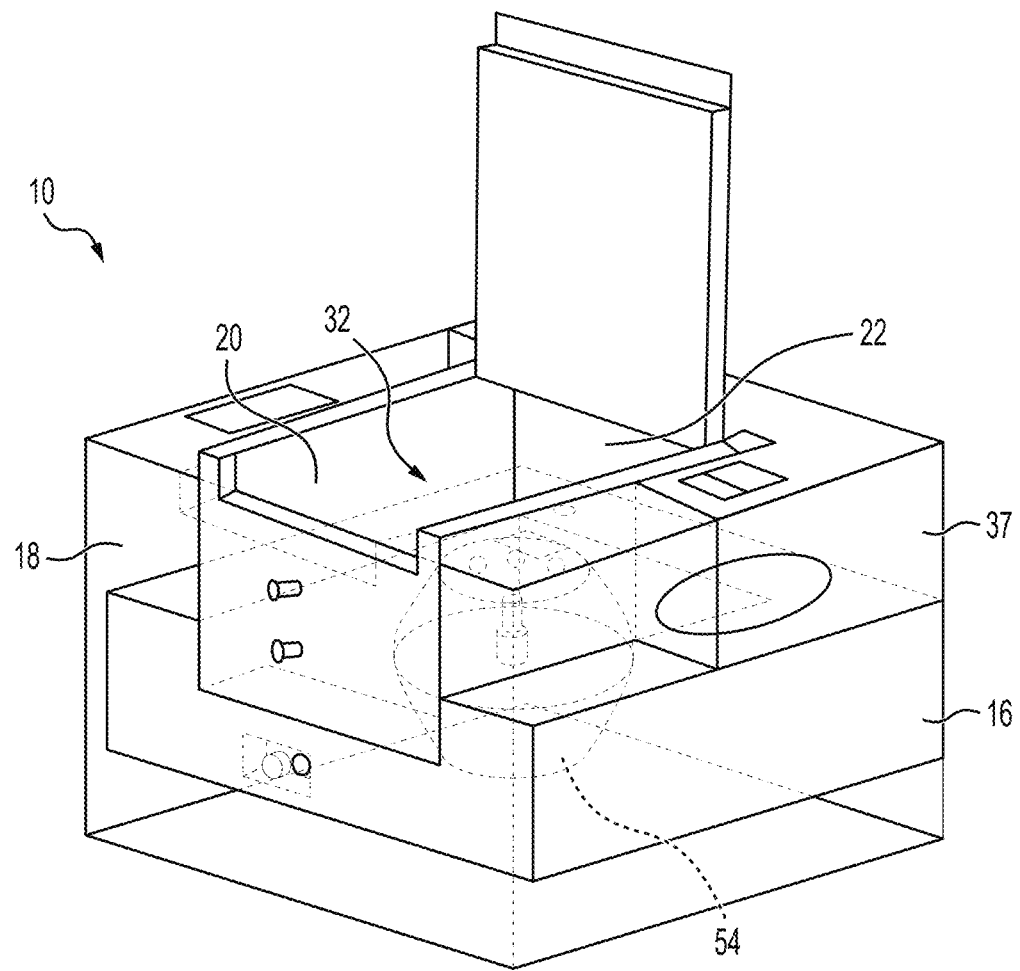
FIG. 3 is a transparent view of the device for autoclaving and centrifuging a sample, showing the centrifuge and water tank.
Figure 5A:
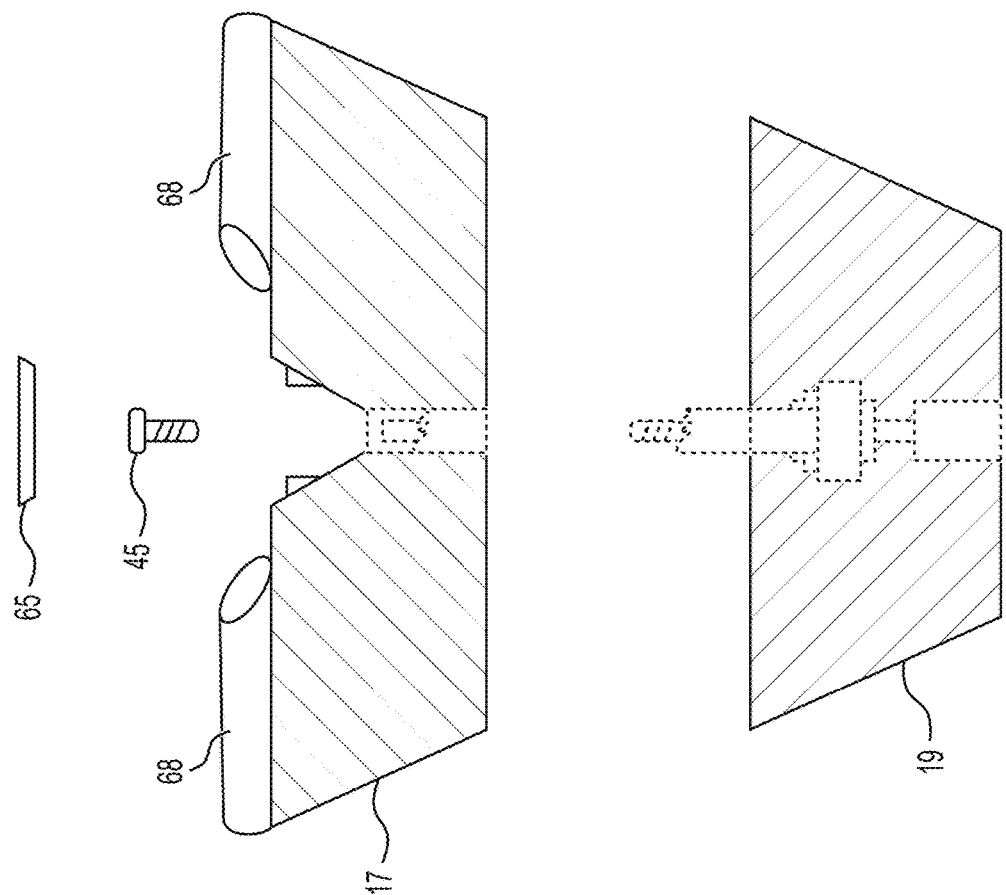
FIG. 5A is an exploded, cross-sectional view of the vertical centrifuge shown in FIG. 4A.
Figure 5B:
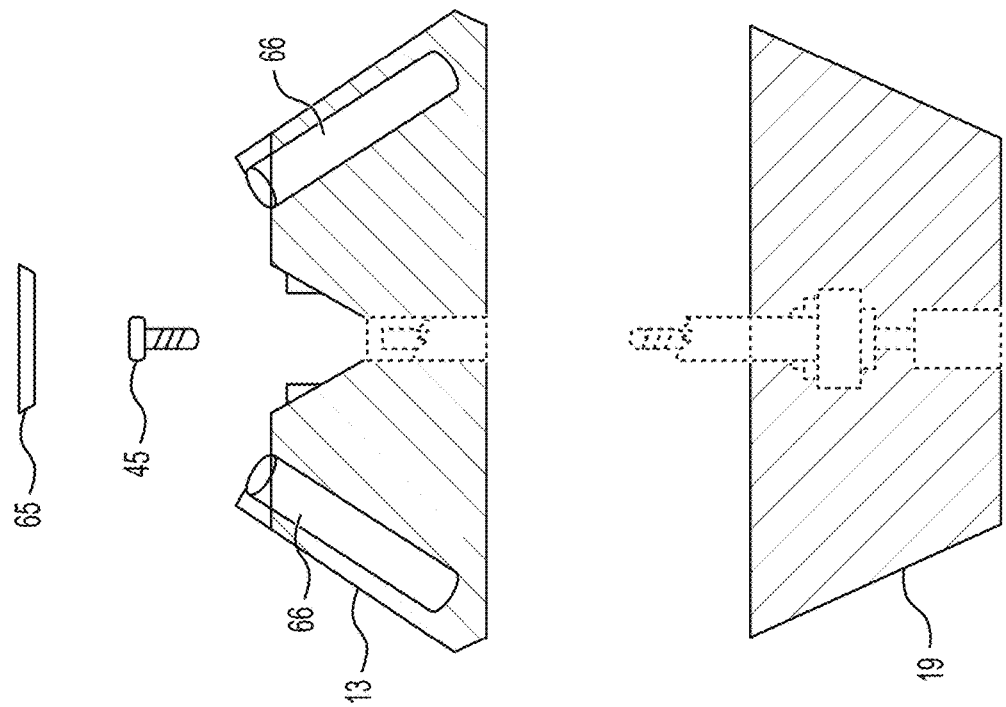
FIG. 5B is an exploded, cross-sectional view of the vertical centrifuge shown in FIG. 4B.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

As shown in FIGS. 1-3, the present subject matter relates to a device for autoclaving and centrifuging a biological sample, designated 10 in the figures. In an embodiment, the biological sample is blood. In an embodiment, the device 10 can heat-treat a blood sample using hot steam while simultaneously centrifuging the blood sample, thereby limiting the duration needed to produce an autoclaved Platelet-Rich Fibrin (PRF). In an embodiment, the device can be used to autoclave various materials, such as medical devices and instruments.

In an embodiment, a device for autoclaving and centrifuging a sample 10 can include a main housing 11 having a base 14, an isolation unit 34 above the base 14, and an interior chamber 32. The main housing 11 can be defined by parallel, horizontal upper and lower side walls 12, 14, and four longitudinal side walls 16, 18, 20, and 22, extending between and connecting the upper and lower side walls 12 and 14, respectively. The isolation unit 34 includes an automated pipe system 35 housed within longitudinal side walls 16, 18, 20, and 22 of the housing 11. The isolation unit 34 surrounds at least a portion of the interior chamber 32. A water tank 37 is disposed within a side wall 16 of the main housing 11 and is in communication with the automated pipe system 35. A centrifuge 54 extends from the base 14 and into the interior chamber 32. A removable autoclave tray 24, secured by clamps, extends from opposing sides of the interior chamber 32. A rotating motor 56 for centrifugation extends into the interior chamber 32 from the centrifuge 54.

In an embodiment, the side wall 20 includes a control panel 41 that is in communication with software configured to operate the automated pipe system 35, a door 36 to optionally allow access into the interior chamber 32, a door button 39 for operating the door 36, and a water intake door 43 that allows access to the water tank 37 housed within longitudinal side wall 16. A pair of handles 30 can be provided on opposing sides of the housing 11.

The automated pipe system 35 within the isolation unit 34 supplies heated steam into the interior chamber 32 for heating the interior chamber 32 until a desired temperature and pressure are achieved in the interior chamber 32. In an embodiment, the desired temperature is about 255° F. to about 275° F., e.g., about 273° F., and the desired pressure ranges from about 15 psi to about 30 psi. Centrifuge 54 can be heat-treated by the hot steam provided in the interior chamber 32 during centrifugation.

The automated pipe system 35 includes a water supply pipe 40 connected to the water tank 37, a water splitter and water supply valve 59 in the water supply pipe 40, a left water pipe 42, a right water pipe 44, a left heating pipe 49 connected to the left water pipe 42, a right heating pipe 48 connected to the right water pipe 44, a steam supply pipe 46 extending between the left heating pipe 49 and right heating pipe 48, chamber pressure/steam seal valve 57, a chamber exhaust pipe 50, chamber exhaust valves 53, 55, a thermometer 25, and pressure gauge 27.

The water supply pipe 40 extends between and connects the left and right water pipes 42, 44 and the water tank 37. The left water pipe 42 is connected to the left heating pipe 46 that extends along one of the longitudinal side walls 20 and the right water pipe 44 is connected to the right heating pipe 48 that extends along an opposite longitudinal side wall 16.

In one embodiment, the water supply valve 59 controls water flow and, when open, directs water equally into the left and right water pipes 42, 44. Water flows from the left and right water pipes 42, 44 into the left and right heating pipes, 49, 48, respectively. The left and right heating pipes 49, 48 transfer electrical energy to water flowing to steam supply pipe 46 so that heated steam is formed and flows into the interior chamber 32 through steam supply pipe 46. In an embodiment, the left and right heating pipes 49, 48 include electrical heating wires for heating. Subsequently, exhaust valves 55, 53 can be opened to allow air inside the chamber 32 to leave through the chamber exhaust pipe 50.

In an embodiment, the centrifuge 54 extends from the housing base 14 and into the interior chamber 32. The centrifuge 54 includes a centrifuge motor cooling fan (not shown), centrifuge base 19, attached to the housing base 14, and a detachable centrifuge insert detachably connected to the centrifuge base with a connector, such as a screw 45. Embodiments of the centrifuge 54 are shown in FIGS. 4A-5B. In an embodiment, the centrifugation insert is a vertical centrifuge insert 13 that is detachably connected to centrifuge base 19. The vertical centrifuge insert 13 can include substantially horizontal vial holders 66 in which the vials including the sample can be disposed. In an embodiment, the centrifuge insert is a horizontal centrifuge insert 17 that is detachably connected to centrifuge base 19. The horizontal centrifuge insert 17 can include substantially horizontal vial holders 68 in which the vials including the sample can be disposed. Once attached to the centrifuge base 19, the centrifugation insert extends into a portion of the interior chamber 32 that is surrounded by the isolation unit 34. The centrifugation motor 56 extends from the centrifugation base 19 through the centrifugation insert.

According to an embodiment, steam flows into the interior chamber 32 from the heat pipes 49, 48 to heat materials, e.g., a sample loaded in the centrifuge or instruments disposed on the tray 24, within the interior chamber 32. The thermometer 25 and pressure gauge 27 are configured to send signals to the control panel 41 when a desired temperature and pressure are achieved in the interior chamber 32, triggering the control panel to seal all of the pipes' valves 53, 55, 57, 59 for a period of time until autoclaving is complete.

In use, the centrifuge tubes are loaded with the desired material and the water tank 37 is filled with water, e.g., distilled water. The desired protocol including, e.g., desired temperature and pressure of the interior chamber 32 and duration of centrifugation, can be set using the control panel 41. The control panel 41 can then send appropriate signals to cause the pipe valves 53, 55, 57, 59 to be sealed to allow a desired temperature and pressure to be maintained in the interior chamber 32 for the desired period of time. The control panel 41 can then send appropriate signals for opening the distilled water splitter and supply valve 59 to allow water to flow from the water tank 37 through the water supply pipe 40 and water pipes 42, 44 and into the heating pipes 49, 48. The heating pipes 49, 48 convert the water into heated steam that then enters the interior chamber 32. The thermometer 25 and pressure gauge 27 monitor the temperature in the interior chamber 32 and send a signal to the control panel 41 when a desired temperature and pressure are achieved in the interior chamber 32. The control panel 41 then sends signals to close the valves 40, 47 once the desired temperature and pressure are achieved in the interior chamber 32. While the pressure and temperature in the interior chamber 32 are maintained for the specified period of time set by the user, the centrifuge motor 56 rotates at the desired speed and time for centrifugation. Afterwards, the device software sends signals to open steam exhaust valves 55, 53 to allow the air inside the chamber 32 to leave through the chamber exhaust pipe 50. Then, the control panel 41 sends signals to unlock the door 36 and unseal button 39 to provide access to the user to press the button 39 to retrieve the samples in the centrifuge 44.

In an embodiment, the sample loaded into centrifuge vials is a blood sample. In an embodiment, the blood can be collected in tubes immediately before centrifugation to minimize the risk of premature clotting or degradation. Once the blood is collected, it is subjected to centrifugation. The tubes can be placed in the centrifuge in a balanced configuration to ensure proper operation.

In an embodiment, vertical PRF centrifugation, using the vertical centrifuge insert, is used for standard PRF preparations. Vertical PRF is more effective when a smaller amount of PRF is sufficient, as the layer formed may be thinner and less concentrated. In another embodiment, horizontal PRF centrifugation, using the horizontal centrifuge insert, is used for modified PRF preparation to maximize platelet and leukocyte concentration by producing thicker and more platelet-rich PRF layers typically. The present device can accommodate either one of the inserts depending on the desired protocol to be used.

The centrifugation protocol depends on the type of PRF being prepared, either as the standard PRF protocol or modified PRF protocols. In an embodiment, the centrifuge is set to a specific speed, measured in revolutions per minute (RPM), runs for a defined duration, and in a specific angulation. Parameters can be selected to achieve the optimal relative centrifugal force (RCF) necessary for separating the blood into its components. In an embodiment, the standard PRF protocol produces a fibrin clot rich in platelets, leukocytes, and growth factors, with RPM ranging between 2700-3000 RPM (200-400×g. RCF) and a centrifugation duration of about 8-12 minutes. In an embodiment, modified PRF protocols (i.e., choukroun, miron) can be run at a range of about 2700-3000 RPM (about 60-400×g RCF) for a duration range of about 3-12 min. Heat-treating the blood using hot steam generated from the heat pipes while centrifugating the blood into platelet-rich fibrin (PRF) can delay degradation and enhance the mechanical properties of the resulting PRF. As is generally known, prolonging the time between blood withdrawal, centrifugation, and heating can harm PRF's effectiveness, leading to less beneficial effects.

It is to be understood that the device for autoclaving and centrifuging a sample is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A device for autoclaving and centrifuging a sample, the device comprising:
    a main housing, the main housing including a housing base, an isolation unit above the housing base and extending within sidewalls of the main housing, and an interior chamber, the isolation unit surrounding at least a portion of the interior chamber;
    a centrifuge including a centrifuge base positioned within the housing base, a centrifuge sample insert positioned in the interior chamber and detachably connected to the centrifuge base, and a centrifuge motor extending through the centrifuge base and centrifuge sample insert;
    a water tank disposed within one of the sidewalls of the main housing;
    an automated pipe system in the isolation unit and connected to the water tank, the automated pipe system configured to supply heated steam into the interior chamber; and
    a computerized control panel in communication with the automated pipe system.

2. The device of claim 1, wherein the automated pipe system includes a left water pipe, a left heat pipe connected to the left water pipe, a right water pipe, a right heat pipe connected to the right water pipe, and a water supply pipe extending between and connecting the water tank to the left and right water pipes, the left and right heat pipes configured to convert water flowing therein into heated steam and direct the heated steam into the interior chamber.

3. The device of claim 1, further comprising a removable tray in the interior chamber.

4. The device of claim 1, further comprising a thermometer gauge in the interior chamber, the thermometer gauge being in communication with the computerized control panel.

5. The device of claim 1, further comprising a pressure gauge in the interior chamber, the pressure gauge being in communication with the computerized control panel.

6. The device of claim 1, wherein the automated pipe system further comprises a chamber exhaust pipe extending into the interior chamber at one end and protruding out of the main housing at another end.

7. The device of claim 1, wherein the centrifuge is a vertical centrifuge.

8. The device of claim 1, wherein the centrifuge is a horizontal centrifuge.

9. A device for autoclaving and centrifuging a sample, comprising:
    a main housing, the main housing including a housing base, an isolation unit above the housing base and extending within sidewalls of the main housing, and an interior chamber, the isolation unit surrounding at least a portion of the interior chamber;
    a thermometer in the interior chamber;
    a centrifuge including a centrifuge base positioned within the housing base, a centrifuge sample insert positioned in the interior chamber and detachably connected to the centrifuge base, and a motor extending through the centrifuge base and centrifuge sample insert;
    a water tank disposed within one of the sidewalls of the main housing;
    an automated pipe system in the isolation unit and connected to the water tank, the automated pipe system configured to supply heated steam into the interior chamber; and
    a computerized control panel in communication with the automated pipe system and the thermometer.

10. The device of claim 9, wherein the automated pipe system includes a left water pipe, a left heat pipe connected to the left water pipe, a right water pipe, a right heat pipe connected to the right water pipe, and a water supply pipe extending between and connecting the water tank to the left and right water pipes, the left and right heat pipes configured to convert water flowing therein into heated steam and direct the heated steam into the interior chamber.

11. The device of claim 9, further comprising a removable tray in the interior chamber.

12. The device of claim 9, further comprising a pressure gauge in the interior chamber, the pressure gauge being in communication with the computerized control panel.

13. The device of claim 9, wherein the automated pipe system further comprises a chamber exhaust pipe extending into the interior chamber at one end and protruding out of the main housing at another end.

14. The device of claim 9, wherein the centrifuge is a vertical centrifuge.

15. The device of claim 9, wherein the centrifuge is a horizontal centrifuge.

* * * * *